(12) United States Patent
Bartling et al.

(10) Patent No.: US 9,028,661 B2
(45) Date of Patent: May 12, 2015

(54) GLUCOSE MEASUREMENT USING A CURRENT SOURCE

(75) Inventors: James E. Bartling, Chandler, AZ (US); Aaron Joel Mach, Gilbert, AZ (US); Darren Edward Noel Wenn, High Wycombe (GB)

(73) Assignee: Microchip Technology Incorporated, Chandler, AZ (US)

( * ) Notice: Subject to any disclaimer, the term of this patent is extended or adjusted under 35 U.S.C. 154(b) by 753 days.

(21) Appl. No.: 13/329,628

(22) Filed: Dec. 19, 2011

(65) Prior Publication Data

US 2012/0171706 A1    Jul. 5, 2012

Related U.S. Application Data

(60) Provisional application No. 61/430,031, filed on Jan. 5, 2011.

(51) Int. Cl.
*G01N 27/327* (2006.01)
(52) U.S. Cl.
CPC .................................. *G01N 27/3273* (2013.01)
(58) Field of Classification Search
CPC ..................... G01N 27/3723; G01N 33/48785
See application file for complete search history.

(56) References Cited

U.S. PATENT DOCUMENTS

| 5,532,602 A | 7/1996 | Wiget | 324/605 |
| 5,832,410 A * | 11/1998 | Lin et al. | 702/22 |
| 6,964,871 B2 * | 11/2005 | Bell et al. | 436/95 |
| 7,468,125 B2 | 12/2008 | Kraft et al. | 205/792 |
| 2002/0146835 A1 | 10/2002 | Modzelewski et al. | 436/95 |
| 2007/0235347 A1 * | 10/2007 | Chatelier et al. | 205/792 |

FOREIGN PATENT DOCUMENTS

| CN | 1996000 A | 7/2007 | C12Q 1/54 |
| EP | 0942278 A2 | 9/1999 | G01N 27/327 |
| EP | 1067384 A2 | 6/2000 | G01N 33/487 |
| GB | 1422172 | 1/1976 | G01N 27/52 |

OTHER PUBLICATIONS

Chinese Office Action, Application No. 201180066855.9, 8 pages, Jun. 5, 2014.
International PCT Search Report and Written Opinion, PCT/US2011/065826, 13 pages, Mar. 16, 2012.

* cited by examiner

*Primary Examiner* — J. Christopher Ball
(74) *Attorney, Agent, or Firm* — King & Spalding L.L.P.

(57) ABSTRACT

A blood glucose meter comprises a blood sample test strip, a constant current source, a precision timer, a digital processor and memory, and an analog measurement circuit, e.g., voltage comparator, analog-to-digital converter (ADC), etc., that eliminates the complex analog front end and other related circuits of present technology glucose meters. When a blood sample is applied to the blood sample test strip a charge, Q, develops from the reaction between an enzyme in the test strip and the blood sample. The constant current source injects a constant current value, I, into the charge, Q, on the blood sample test strip over a precisely measured time determined by when the excess charge, Q, has been removed from the test strip. The amount of charge, Q, is determined by $Q=I*T$, the charge, Q, is then converted into a blood glucose level for display.

34 Claims, 7 Drawing Sheets

GLUCOSE MEASUREMENT USING A CURRENT SOURCE

RELATED PATENT APPLICATION

This application claims priority to commonly owned U.S. Provisional Patent Application Ser. No. 61/430,031; filed Jan. 5, 2011; entitled "Glucose Measurement Using a Current Source," by James E. Bartling, Aaron Joel Mach and Darren Edward Noel Wenn; which is hereby incorporated by reference herein for all purposes.

TECHNICAL FIELD

The present disclosure relates to blood glucose measurement equipment, i.e., a glucose meter for measuring glucose in a blood sample, and, more particularly, to using a controlled current source, time measurement device and voltage comparator or analog-to-digital converter (ADC) in determining the amount of glucose in the blood sample.

BACKGROUND

For diabetics it is necessary to monitor blood glucose levels. Blood glucose level is measured with blood glucose measurement equipment, i.e., a glucose meter. The glucose meter uses a chemical reaction to generate a charge of free electrons when the blood glucose reacts with an enzyme. The amount of free charge generated is proportional to the blood glucose level. The amount of charge on the blood sample strip is measured and then the measured value of charge is used in determining the level of glucose in the blood sample. Presently, the glucose meter requires a complex analog front end with multiple precision operational amplifiers and voltage references. This makes the glucose meters expensive, complicated and requires calibration or replacement more often then desired. With the increase in diabetics due to obesity and other factors in today's societies, the use of glucose meters has greatly increased, and replacement and upgraded models of glucose meters are selling in the millions each year.

SUMMARY

Therefore it would be desirable in a glucose meter to eliminate the need for precision analog circuits such as operational amplifiers, precision voltage references, high resolution ADCs and complex digital computations in determining the glucose level in a blood sample.

According to an embodiment, a method for measuring glucose in a blood sample may comprise the steps of: a) connecting a constant current source having a constant current value to a blood sample test strip; b) introducing a blood sample onto the blood sample test strip; c) reacting the blood sample with an enzyme in the blood sample test strip to produce a charge, Q, on the blood sample test strip; d) measuring a voltage on the blood sample test strip in determining a voltage value thereof; e) determining whether the voltage value of the voltage on the blood sample test strip has significantly decreased from a first voltage value, wherein e1) if the voltage value has not significantly decreased from the first voltage value then return to step d), and e2) if the voltage value has significantly decreased from the first voltage value then continue to step f); f) disconnecting the constant current source from the blood sample test strip; g) waiting a soak time; h) starting a timer to determine a charge removal time after the soak time is over; i) reconnecting the constant current source to the blood sample test strip; j) measuring the voltage on the blood sample test strip in determining the voltage value thereof; k) determining whether the voltage value of the voltage on the blood sample test strip has significantly increased from a second voltage value, wherein k1) if the voltage value has not significantly increased from the second voltage value then return to step j), and k2) if the voltage value has significantly increased from the second voltage value then stop the timer and continue to step l); l) determining a charge value of the charge on the blood sample test strip by multiplying the charge removal time and the constant current value; and m) determining a blood glucose level (BGL) from the charge value. According to a further embodiment of the method, the BGL is displayed on a visual display. According to a further embodiment of the method, the step of determining the BGL from the charge value comprises the steps of looking up the charge value in a look-up table and reading a corresponding BGL value therefrom. According to a further embodiment of the method, the soak time is about one (1) second. According to a further embodiment of the method, the soak time is less than one (1) second. According to a further embodiment of the method, the soak time is from about one (1) second to about five (5) seconds.

According to another embodiment, a method for measuring glucose in a blood sample may comprise the steps of: a) connecting a constant current source having a constant current first value to a blood sample test strip; b) introducing a blood sample onto the blood sample test strip; c) reacting the blood sample with an enzyme in the blood sample test strip to produce a charge, Q, on the blood sample test strip; d) measuring a voltage on the blood sample test strip in determining a voltage value thereof; e) determining whether the voltage value of the voltage on the blood sample test strip has significantly decreased from a first voltage value, wherein e1) if the voltage value has not significantly decreased from the first voltage value then return to step d), and e2) if the voltage value has significantly decreased from the first voltage value then continue to step f); f) waiting a soak time; g) starting a timer to determine a charge removal time after the soak time is over; h) increasing the constant current first value to a constant current second value; i) measuring the voltage on the blood sample test strip in determining the voltage value thereof; j) determining whether the voltage value of the voltage on the blood sample test strip has significantly increased from a second voltage value, wherein j1) if the voltage value has not significantly increased from the second voltage value then return to step i), and j2) if the voltage value has significantly increased from the second voltage value then stop the timer and continue to step k); k) determining a charge value of the charge on the blood sample test strip by multiplying the charge removal time and the constant current value; and l) determining a blood glucose level (BGL) from the charge value.

According to a further embodiment of the method, the BGL is displayed on a visual display. According to a further embodiment of the method, the step of determining the BGL from the charge value comprises the steps of looking up the charge value in a look-up table and reading a corresponding BGL value therefrom. According to a further embodiment of the method, the soak time is about one (1) second. According to a further embodiment of the method, the soak time is less than one (1) second. According to a further embodiment of the method, the soak time is from about one (1) second to about five (5) seconds.

According to yet another embodiment, an apparatus for measuring glucose in a blood sample may comprise: a blood sample test strip having an enzyme that reacts with glucose in a blood sample to produce a charge; an analog-to-digital converter (ADC) coupled to the blood sample test strip; a digital processor and memory coupled to the ADC; a timer for measuring a charge removal time, the timer is coupled to the digital processor; a constant current source having a constant current value; and a switch coupled between the constant current source and the blood sample test strip, and controlled by the digital processor, wherein the switch is normally closed; wherein when a blood sample is taken onto the blood sample test strip a voltage across the blood sample test strip changes from a high level to a low level, the switch opens thereby disconnecting the constant current source from the blood sample test strip, the switch remains open for a soak time, and after the soak time has elapsed the timer starts measuring the charge removal time and the switch closes thereby reconnecting the constant current source to the blood sample test strip; wherein the ADC samples the voltage across the blood sample test strip until the voltage substantially increases then the timer stops measuring the charge removal time; and the digital processor calculates the charge that was on the blood sample test strip by multiplying the constant current value with the charge removal time.

According to a further embodiment, the digital processor converts the calculated charge to a blood glucose level (BGL). According to a further embodiment, a display is coupled to the digital processor and displays the BGL. According to a further embodiment, a charge-to-BGL look-up table is stored in the memory and used by the digital processor to convert the calculated charge to the BGL. According to a further embodiment, a constant current source having a plurality of programmable constant current values is controlled by the digital processor. According to a further embodiment, the ADC, digital processor and memory, timer, constant current source and switch are fabricated on an integrated circuit. According to a further embodiment, the integrated circuit comprises a mixed signal analog and digital microcontroller integrated circuit. According to a further embodiment, the digital processor is a microcontroller. According to a further embodiment, the soak time is about one (1) second. According to a further embodiment, the soak time is less than one (1) second. According to a further embodiment, the soak time is from about one (1) second to about five (5) seconds.

According to still another embodiment, an apparatus for measuring glucose in a blood sample may comprise: a blood sample test strip having an enzyme that reacts with glucose in a blood sample to produce a charge; an analog-to-digital converter (ADC) coupled to the blood sample test strip; a digital processor and memory coupled to the ADC; a timer for measuring a charge removal time, the timer is coupled to the digital processor; and a constant current source coupled to the blood sample test strip and the digital processor, wherein the constant current source comprises a plurality of programmable constant current values controlled by the digital processor; wherein the constant current source is at a low constant current value, a blood sample is taken onto the blood sample test strip, the constant current source remains at the low constant current value until a voltage across the blood sample test strip changes from a high level to a low level, then the constant current source changes to a higher constant current value and the timer starts measuring the charge removal time, and the ADC samples the voltage across the blood sample test strip until the voltage substantially increases then the timer stops measuring the charge removal time; and the digital processor calculates the charge that was on the blood sample test strip by multiplying the higher constant current value with the charge removal time.

According to a further embodiment, the digital processor converts the calculated charge to a blood glucose level (BGL). According to a further embodiment, a display is coupled to the digital processor and displays the BGL. According to a further embodiment, a charge-to-BGL look-up table is stored in the memory and used by the digital processor to convert the calculated charge to the BGL. According to a further embodiment, the ADC, digital processor and memory, timer and constant current source are fabricated on an integrated circuit. According to a further embodiment, the integrated circuit comprises a mixed signal analog and digital microcontroller integrated circuit. According to a further embodiment, the digital processor is a microcontroller. According to a further embodiment, the constant current source remains at a low constant current value for a soak time after the voltage across the blood sample test strip changes from the high level to the low level. According to a further embodiment, the soak time is about one (1) second. According to a further embodiment, the soak time is less than one (1) second. According to a further embodiment, According to a further embodiment, the soak time is from about one (1) second to about five (5) seconds.

BRIEF DESCRIPTION OF THE DRAWINGS

A more complete understanding of the present disclosure may be acquired by referring to the following description taken in conjunction with the accompanying drawings wherein.

While the present disclosure is susceptible to various modifications and alternative forms, specific example embodiments thereof have been shown in the drawings and are herein described in detail. It should be understood, however, that the description herein of specific example embodiments is not intended to limit the disclosure to the particular forms disclosed herein, but on the contrary, this disclosure is to cover all modifications and equivalents as defined by the appended claims.

DETAILED DESCRIPTION

A blood glucose meter comprises a blood sample test strip, a constant current source, a precision timer, a digital processor and memory, and an analog measurement circuit, e.g., voltage comparator, analog-to-digital converter (ADC), etc., that eliminates the complex analog front end and other related circuits of present technology glucose meters. When a blood sample is applied to the blood sample test strip a charge, Q, develops from the reaction between an enzyme in the test strip and the blood sample. The constant current source injects a constant current value, I, into the charge, Q, on the blood sample test strip over a precisely measured time determined when the excess charge, Q, has been removed from the test strip. The precisely measured time is measured by the precision timer. The amount of charge, Q, is determined by Q=I*T, the charge, Q, is then converted into a blood glucose level for display.

The ADC samples voltages across the blood sample test strip and converts the sampled voltages to digital representations thereof. The digital representations of the voltage samples are sent to the digital processor for further processing. Before a blood sample is taken with the blood sample test strip, the test strip is at substantially an infinite (very high) resistance since there is not yet an electron charge formed from the enzyme reacting with the glucose in the blood sample. The blood sample test strip may be characterized as a voltage source in parallel with a very high resistance.

The constant current source is initially coupled to the blood sample test strip before a blood sample is taken. Since an unused blood sample test strip is a very high resistance, the voltage across the test strip will approach a power supply voltage, e.g., $V_{DD}$. The blood sample test strip is further coupled to the glucose meter ADC. When a sample of blood is taken on the test strip an enzyme in the test strip reacts with the glucose in the blood to generate charge and the resistance between the terminals of the blood sample test strip drops significantly which pulls down on end of the constant current source and input of the ADC or comparator closer to $V_{SS}$ then to $V_{DD}$. This voltage drop signifies the start of a glucose determination cycle in the glucose meter.

The digital processor determines from the digital representations of the voltage samples from the ADC or comparator that a significant voltage drop across the test strip has occurred. The digital processor may disconnect the constant current source from the test strip for a certain "soak" time, e.g., less than (1) second, about one (1) second, one (1) to five (5) seconds, etc., depending upon the chemical reaction requirements of the blood sample and the enzyme in the test strip. Once the soak time has expired, the digital processor reconnects the constant current source to the test strip to begin removing the excess charge in the test strip. The sampled voltages during the excess charge removal time remain closer to $V_{SS}$ then to $V_{DD}$. However once most of the charge on the test strip has been removed by the constant current source, the voltage on the test strip will go back toward $V_{DD}$, but not all the way to $V_{DD}$.

This jump in the voltage across the test strip toward $V_{DD}$ signifies completion of the glucose determination cycle. Using the equation Q=I*T where Q is the charge, I is the constant current value, and T is the amount of time needed to remove the charge from the blood sample test strip, the digital processor then multiplies the constant current value with the time value to come up with the amount of charge that was on the blood sample test strip. Once this charge has been determined, a table look-up may be used to present an accurate blood glucose level (BGL) of the test subject's blood.

The precision timer may be started when a significant voltage drop across the test strip is detected or when the constant current source is reconnected to the test strip, e.g., after the soak time has elapsed. For certain blood sample test strip chemistries the constant current source need not be decoupled from the test strip, only set to a minimum current value. Then after the soak time has elapsed, the current value from the constant current source may be increased. The digital processor may also display this blood glucose level (BGL) on a display to be read by the person being tested for blood sugar (glucose) and/or the health care professional.

A substantial reduction in the need for precision analog components makes a more affordable and long term reliable glucose meter possible. By using this constant current-time measurement for determining blood glucose levels, manufacturers can reduce the cost and improve the long term accuracy of a much less complicated glucose meter.

An accurate constant current source, time measurement and voltage level detection may be provided by, for example but not limited to, a charge time measurement unit (CTMU), timer, ADC and digital processor in a microcontroller integrated circuit. The CTMU is more fully described in Microchip application notes AN1250 and AN1375, available at www.microchip.com, and commonly owned U.S. Pat. Nos. 7,460,441 B2, entitled "Measuring a long time period;" and 7,764,213 B2, entitled "Current-time digital-to-analog converter," both by James E. Bartling; wherein all are hereby incorporated by reference herein for all purposes.

The test strip can be any suitable glucose test strip available from multiple vendors. The test strip provides the chemical reaction with the glucose in a blood sample to generate a charge (surplus of electrons). The amount of charge generated is dependent on the amount of glucose in the blood sample. It is this charge that must be measured to determine the blood glucose level. The CTMU provides a fixed constant current source. The ADC measures the voltage across the test strip. The measurement of actual charge is done by removing the charge at a fixed rate as determined by the constant current source and measuring the time that it takes to remove the charge. Time may be measured using a simple digital timer of a digital processor, e.g., microcontroller that may also comprise the CTMU, and the ADC and/or voltage comparator.

It is further contemplated and within the scope of this disclosure that the amount of voltage drop across the test strip may be used in determining selection of a constant current value from a programmable constant current source. For example, a greater voltage change (drop) indicates a larger charge of electrons from the blood-enzyme reaction because of a high level of glucose in the blood. In this case, a programmable constant current source may be controlled by the digital processor to increase its constant current value so that the completion of the glucose determination cycle may be shorter in time. However, the shorter the completion time of the glucose determination cycle the less accurate will be the results. But with a high BGL concentration high accuracy is of less significance. With lower BGL values a longer time glucose determination cycle will result in a more actuate determination of the BGL value.

Blood sample test strips having different chemistries (enzymes) will require different operating characteristics for the application of the constant current values from the constant current source and look-up tables to convert the calculated charge, Q, to a respective BGL number for display. The glucose meter may have different sockets adapted for different types of blood sample test strips, and/or at least one blood sample test strip socket may have additional inputs that may be used to decode the type of test strip inserted therein so that the correct calculation algorithm can be automatically selected by the digital processor in controlling the constant current source coupling to the test strip, any soak time requirements, and specific charge, Q, to BGL look-up tables used.

Referring now to the drawings, the details of specific example embodiments are schematically illustrated. Like elements in the drawings will be represented by like numbers, and similar elements will be represented by like numbers with a different lower case letter suffix.

Figure 1:
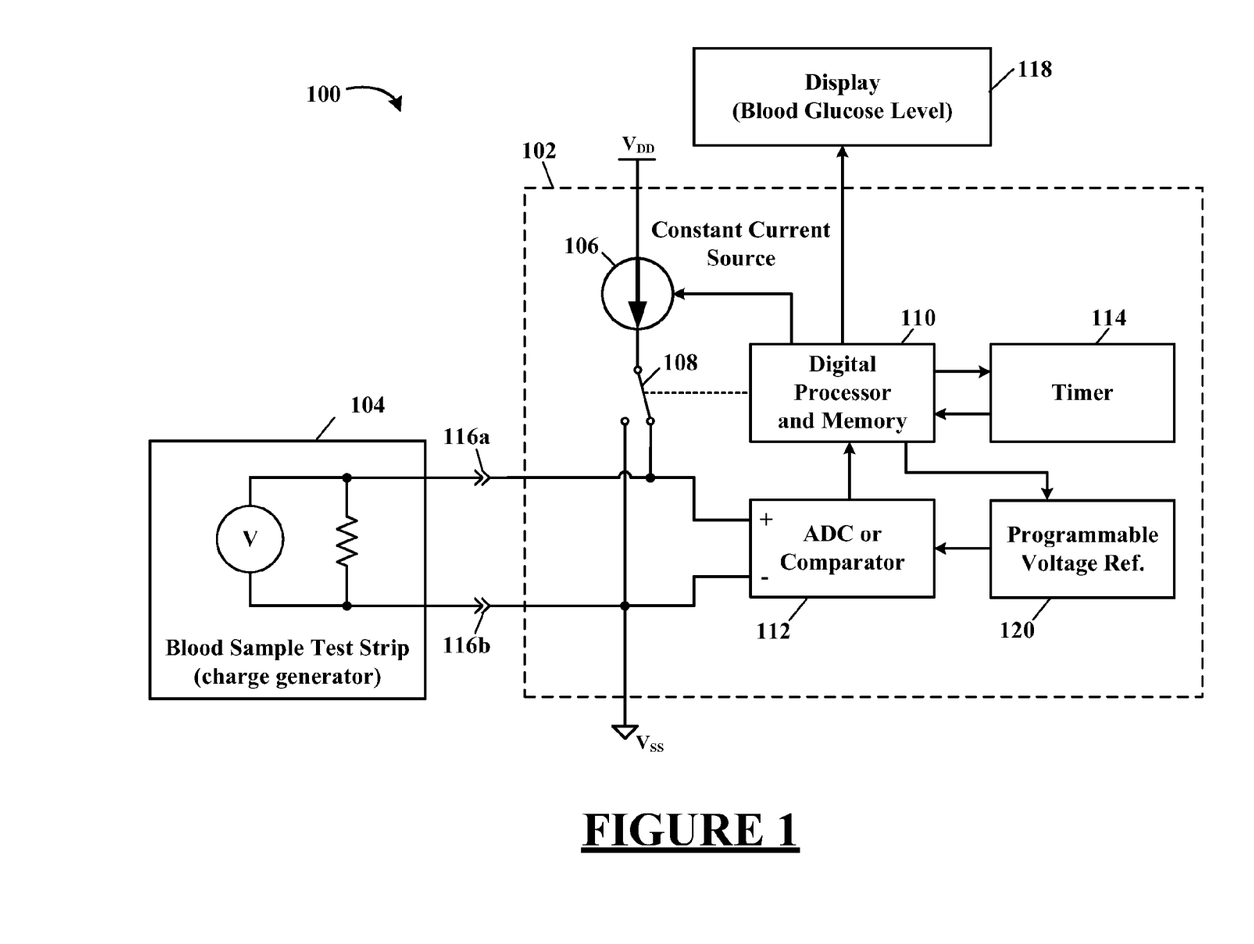
FIG. 1 illustrates a schematic block diagram of a blood glucose measurement device, according to a specific example embodiment of this disclosure.

Referring to FIG. 1, depicted is a schematic block diagram of a blood glucose measurement device, according to a specific example embodiment of this disclosure. A blood glucose measurement device, generally represented by the numeral 100, comprises a blood sample test strip 104, a constant current source 106, a switch 108, a digital processor and memory 110, an analog-to-digital converter (ADC) 112 (may also be a comparator), timer 114, terminals 116 and a display 118. The digital processor 110 may be, for example but is not limited to, a microcontroller, a microprocessor, a digital signal processor (DSP), a programmable logic array (PLA), an application specific integrated circuit (ASIC), etc. The memory of the digital processor 110 may be volatile and/or non-volatile memory. A software and/or firmware operating program, and blood glucose level look-up table(s) may be stored in the memory coupled to the digital processor 110. The display 118 may be, for example but is not limited to, a liquid crystal display, an light emitting diode (LED) display, etc.

A sample of blood from a test subject is placed onto the blood sample test strip 104 where an enzyme therein reacts with the blood sample to create an electron charge across the terminals 116a and 116b. The blood sample test strip 104 is a one use item and is removable from the rest of the blood glucose measurement system 100 via the terminals 116 after the blood glucose level in the blood has been determined and a new blood sample is to be taken. A programmable voltage reference 120 may be used when a voltage comparator 112 is used in stead of an ADC for voltage determination, and may be controlled by the digital processor 110. The ADC (or comparator) 112 may have a single ended input or differential inputs.

The ADC 112 samples voltages across the blood sample test strip 104 and converts the sampled voltages to digital representations thereof. The digital representations of the voltage samples are sent to the digital processor 110 for further processing. Before a blood sample is taken with the blood sample test strip 104, the test strip 104 is at substantially an infinite (very high) resistance since there is not yet an electron charge formed from the enzyme reacting with the glucose in the blood sample. The blood sample test strip 104 may be characterized as a two electrical terminal device.

The constant current source 106 is initially coupled to the blood sample test strip 104 before a blood sample is taken. Since an unused blood sample test strip 104 is a very high resistance, the voltage across the test strip 104 will approach a power supply voltage, e.g., $V_{DD}$. The blood sample test strip 104 is further coupled to the ADC 112. When a sample of blood is taken on the test strip 104 an enzyme in the test strip 104 reacts with the glucose in the blood and the resistance between the terminals 116 drops significantly and pulls down one end of the constant current source 104 and input of the ADC 112 (or comparator) closer to $V_{SS}$ then to $V_{DD}$. This voltage drop signifies the start of a glucose determination cycle in the glucose meter 100.

The digital processor 110 determines from the digital representations of the voltage samples from the ADC 112 (or comparator) that a significant voltage drop across the test strip 104 has occurred. The digital processor may 110 disconnect the constant current source 106 from the test strip 104 with the switch 108 for a certain "soak" time, a certain "soak" time, e.g., less than (1) second, about one (1) second, one (1) to five (5) seconds, etc., depending upon the chemical reaction requirements of the blood sample and the enzyme in the test strip. Once the soak time has expired, the digital processor 110 reconnects the constant current source 106 with the switch 108 to the test strip 104 to begin removing the excess charge in the test strip 104. The sampled voltages during the excess charge removal time remain closer to $V_{SS}$ then to $V_{DD}$. However once most of the charge on the test strip 104 has been removed by the constant current source 106, the voltage on the test strip 104 will go back toward $V_{DD}$, but not all the way to $V_{DD}$.

This jump in the voltage across the test strip 104 toward $V_{DD}$ signifies completion of the glucose determination cycle. Using the equation Q=I*T where Q is the charge, I is the constant current value, and T is the amount of time needed to remove the charge from the blood sample test strip, the digital processor 110 then multiplies the constant current value of the constant current source 106 with the time value from the timer 114 to come up with the amount of charge that was on the blood sample test strip 104. Once this charge has been determined, a table look-up in the memory of the digital processor 110 may be used to present an accurate blood glucose level (BGL) of the test subject's blood on the display 118.

The timer 114 may be started when a significant voltage drop across the test strip 104 is detected or when the constant current source 106 is reconnected to the test strip 104, e.g., after the soak time has elapsed. For certain blood sample test strip chemistries the constant current source need not be decoupled from the test strip, only set to a minimum current value. Then after the soak time has elapsed, the current value from the constant current source may be increased. The digital processor 110 may also display this blood glucose level (BGL) on the display 118 to be read by the person being tested for blood sugar (glucose) and/or the health care professional.

It is further contemplated and within the scope of this disclosure that the amount of voltage drop at the test strip terminals 116 (voltage drop depends on amount of charge, Q, generated by the reaction of the enzyme with the blood sample) may be used in determining selection of a constant current value from a programmable constant current source 106. For example, a greater voltage change (drop) indicates a larger charge of electrons from the blood-enzyme reaction because of a high level of glucose in the blood. In this case, a programmable constant current source 106 may be controlled by the digital processor 110 to increase its constant current value so that the completion of the glucose determination cycle may be shorter in time. However, the shorter the time of completion of the glucose determination cycle the less accurate will be the results. But with a high BGL concentration less accuracy is of lower significance. With lower BGL values a longer time glucose determination cycle will result in a more actuate determination of the BGL value.

It is further contemplated and within the scope of this disclosure that a programmable comparator (e.g., having a programmable voltage reference 120) may be used in place of the ADC 112, and that the digital processor 110 may dynamically program different voltage reference values based upon the voltage characteristics of the test strip 104 over the various events after taking the blood sample as more fully described hereinabove.

Blood sample test strips 104 having different chemistries (enzymes) will require different operating characteristics for the application of constant current values from the constant current source and look-up tables to convert the calculated charge, Q, to a respective BGL number for display. The glucose meter 100 may have different sockets adapted for different types of blood sample test strips (not shown), and/or at least one blood sample test strip socket (not shown) may have additional inputs that may be used to decode the type of test strip inserted therein so that the correct calculation algorithm can be automatically selected by the digital processor 110 in controlling the constant current source 106 coupling to the test strip 104, any soak time requirements, and specific charge, Q, to BGL look-up tables used.

Figure 2:
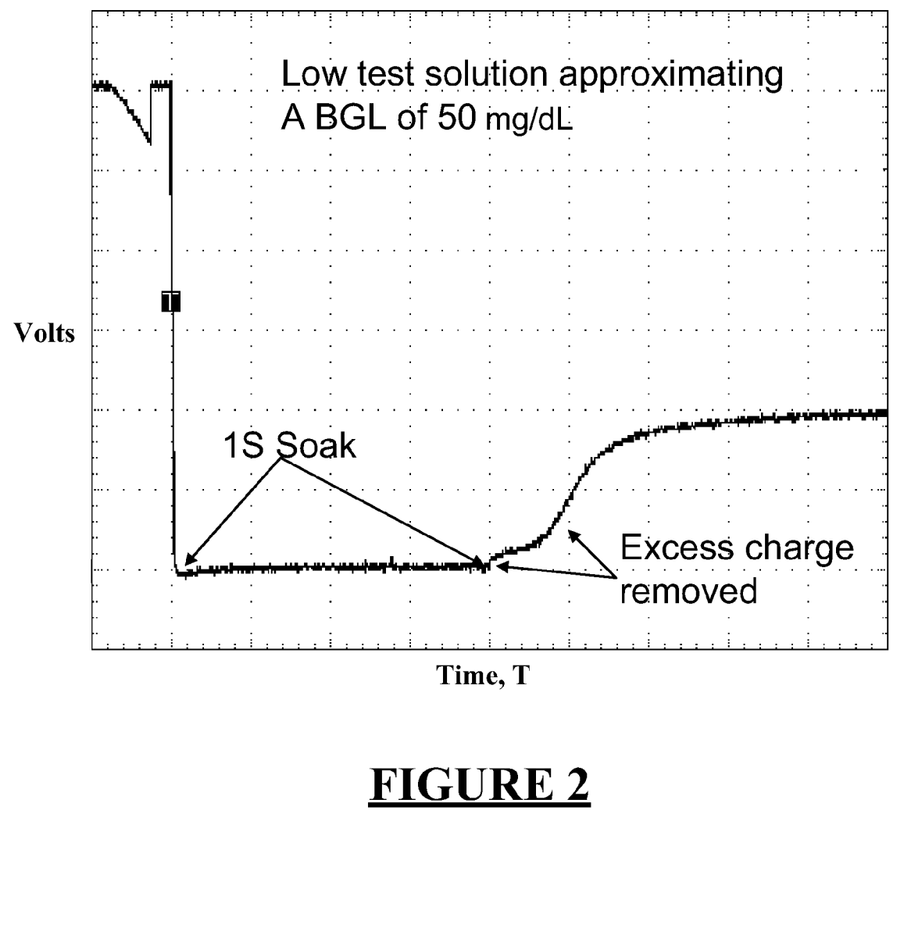
FIG. 2 illustrates a charge-time graph of a low test solution approximating a BGL of 50 mg/dL, according to the teachings of this disclosure.

Referring to FIGS. 2-5, depicted are various charge-time graphs of test solutions approximating various blood glucose levels (BGLs) tested by the blood glucose measurement system, according to the teachings of this disclosure. FIG. 2 illustrates a charge-time graph of a test solution approximating a BGL of 50 mg/dL. The one (1) second soak time begins after a significant drop in the voltage across the test strip 104. After the soak time, excess charge is removed by connecting the constant current source 106 to the test strip 104 until there is a jump toward $V_{DD}$ in the voltage across the test strip 104. Since this graph represents a very low glucose level in the blood there is not as much charge generated by the blood and enzyme reaction, and not that much current from the constant current source needs to be injected into the test strip 104 to end the glucose determination cycle. Also the glucose determination cycle is not that long relative to the soak time.

Figure 3:
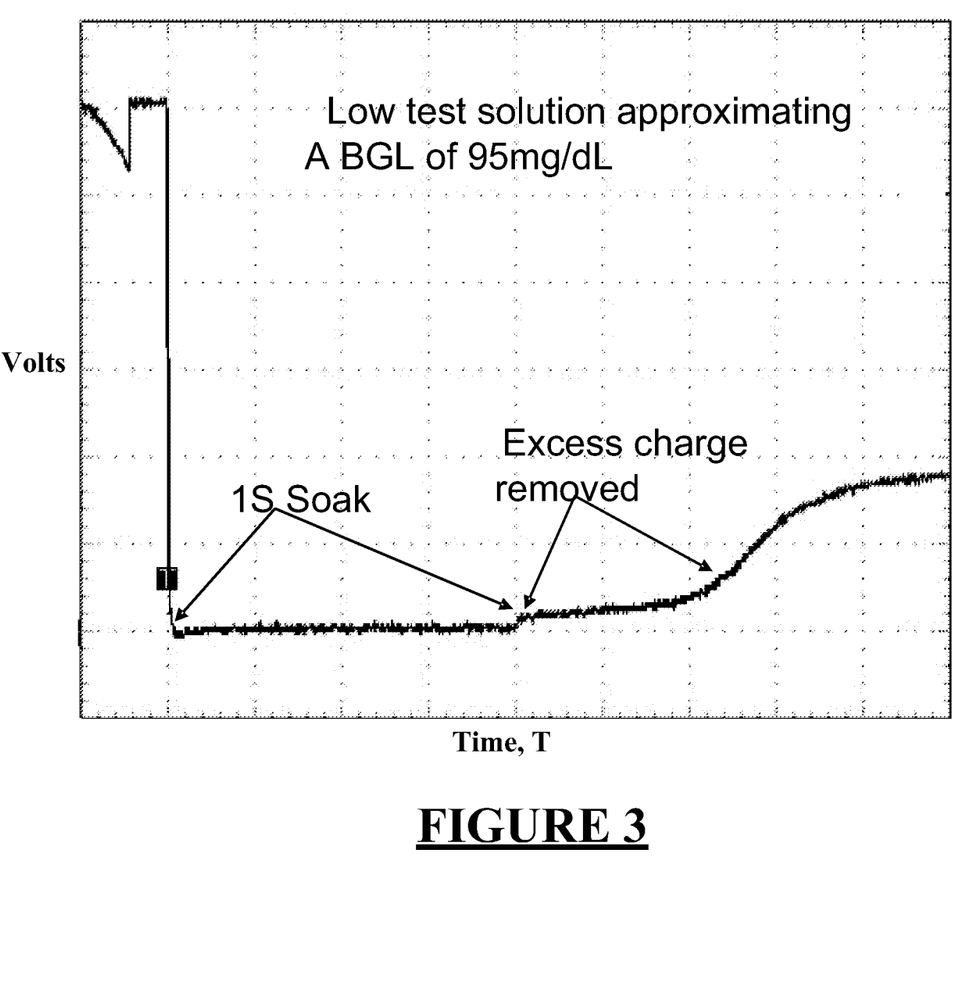
FIG. 3 illustrates a charge-time graph of a low test solution approximating a BGL of 95 mg/dL, according to the teachings of this disclosure.

FIG. 3 illustrates a charge-time graph of a test solution approximating a BGL of 95 mg/dL. The one (1) second soak time begins after a significant drop in the voltage across the test strip 104. After the soak time, excess charge is removed by connecting the constant current source 106 to the test strip 104 until there is a jump toward $V_{DD}$ in the voltage across the test strip 104. The graph of FIG. 3 represents a slightly higher glucose level in the blood then that shown in FIG. 2, and therefore requires that the constant current source 106 be connected to the test strip 104 for a longer period of time.

Figure 4:
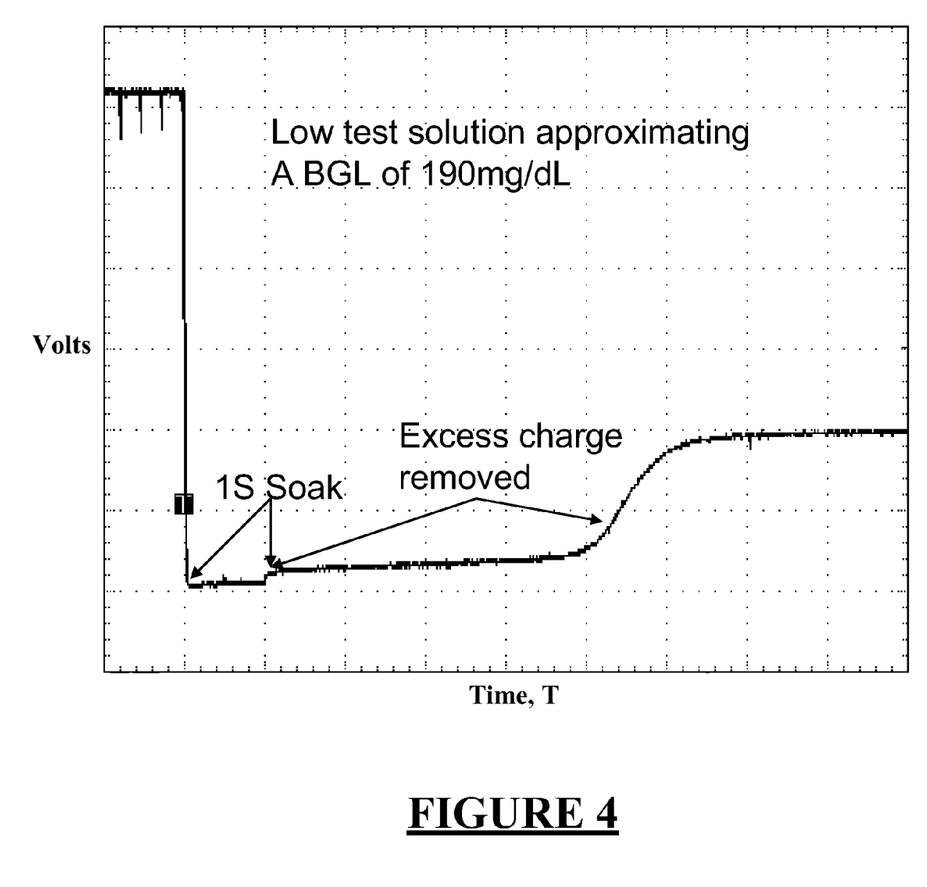
FIG. 4 illustrates a charge-time graph of a low test solution approximating a BGL of 190 mg/dL, according to the teachings of this disclosure.

Referring to FIG. 4, depicted is a charge-time graph of a test solution approximating a BGL of 190 mg/dL. The one (1) second soak time begins after a significant drop in the voltage across the test strip 104. After the soak time, excess charge is removed by connecting the constant current source 106 to the test strip 104 until there is a jump toward $V_{DD}$ in the voltage across the test strip 104. The graph of FIG. 4 represents higher glucose levels in the blood then those shown in FIGS. 2 and 3, and therefore requires that the constant current source 106 be connected to the test strip 104 for a longer period of time.

Figure 5:
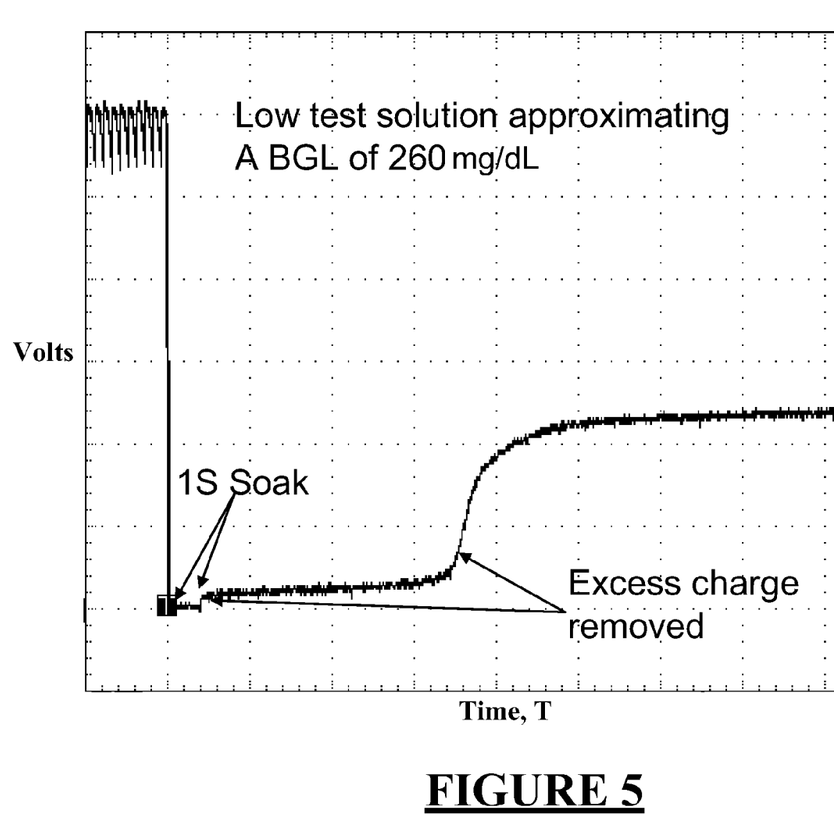
FIG. 5 illustrates a charge-time graph of a low test solution approximating a BGL of 260 mg/dL, according to the teachings of this disclosure.

Referring to FIG. 5, depicted is a charge-time graph of a low test solution approximating a BGL of 260 mg/dL. The one (1) second soak time begins after a significant drop in the voltage across the test strip 104. After the soak time, excess charge is removed by connecting the constant current source 106 to the test strip 104 until there is a jump toward $V_{DD}$ in the voltage across the test strip 104. The graph of FIG. 5 represents a much higher glucose level in the blood then those shown in FIGS. 2 and 3, and therefore requires that the constant current source 106 be connected to the test strip 104 for a much longer period of time. However for this high of a glucose level in the blood, a higher constant current value from a programmable constant source 106 may be used to shorten the time required for the glucose determination cycle to complete. The accuracy of the BGL will not be as good as when using the lower constant current value, but with a longer time for the glucose determination cycle.

Figure 6:
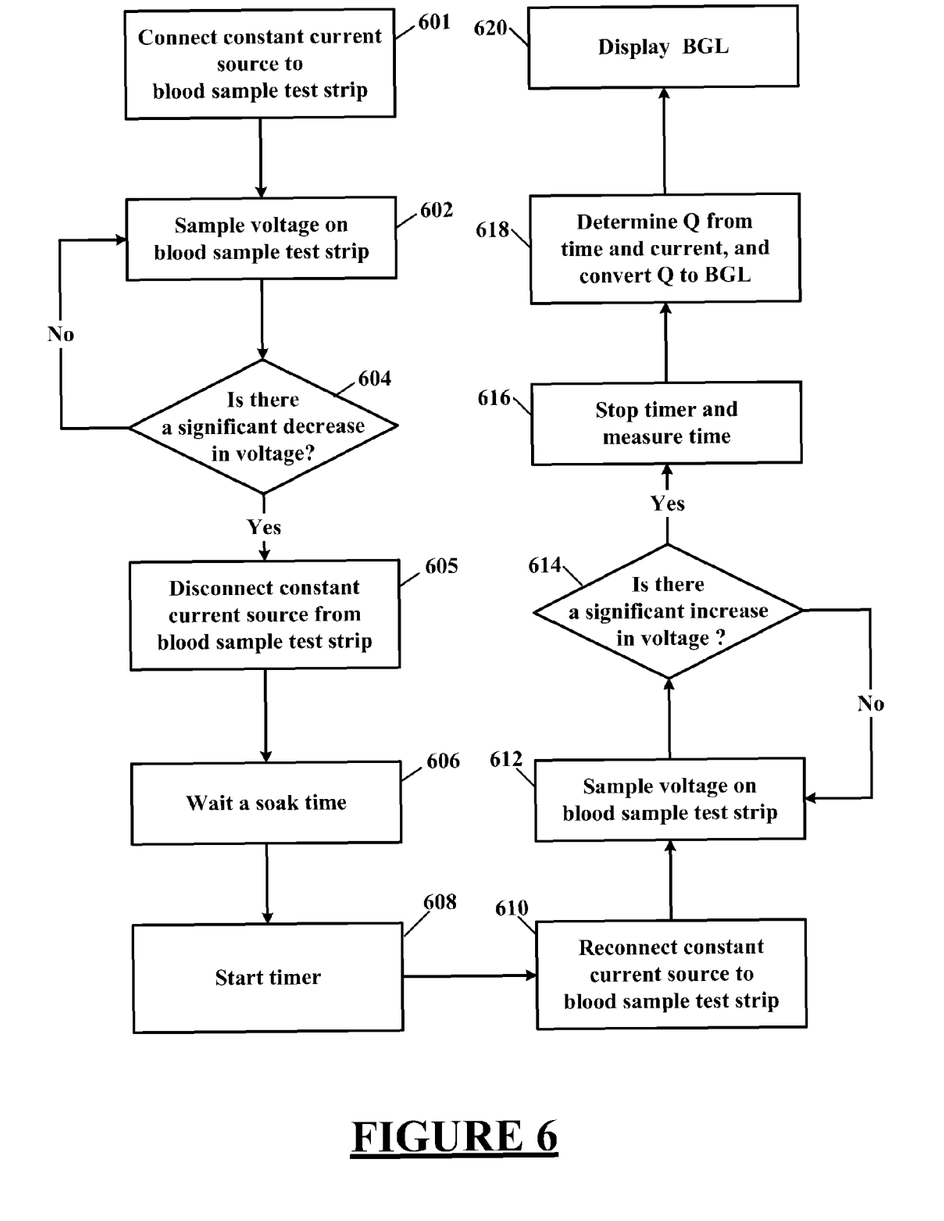
FIG. 6 illustrates a schematic flow diagram of a method for measuring blood glucose, according to another specific example embodiment of this disclosure.

Referring to FIG. 6, depicted is a schematic flow diagram of a method for measuring blood glucose, according to another specific example embodiment of this disclosure. In step 601 a constant current source 106 is connected to a blood sample test strip 104. In step 602 a voltage sample of the test strip 104 is taken by the ADC 112 which converts this voltage sample to a digital representation thereof, the digital processor 110 reads the digital representation and stores it into the memory 110. In step 604 a comparison is made of the voltage sample just taken to a prior sampled voltage (digital representation thereof stored in the memory 110) of the test strip 104. If there is not a significant decrease in the value of the voltage sample then another voltage sample is taken by the ADC 112. However, if there is a significant decrease in the value of the voltage sample then in step 605 the constant current source 106 is disconnected from the test strip 104, wherein the constant current source 106 remains disconnected from the test strip 104 for a soak time determined in step 606. Once the soak time is over step 608 starts a timer 114, and in step 610 the constant current source 106 is reconnected to the test strip 104.

In step 612 another voltage sample of the test strip 104 is taken by the ADC 112 which converts this voltage sample to a digital representation thereof, the digital processor 110 reads this digital representation and stores it into the memory 110. In step 614 a comparison is made of the voltage sample just taken to a prior sampled voltage (digital representation thereof stored in the memory 110) of the test strip 104. If there is not a significant increase in the value of the voltage sample then another voltage sample is taken by the ADC 112. However, if there is a significant increase in the value of the voltage sample then in step 616 the timer 114 is stopped and the time elapsed therein is measured. In step 618 the amount of charge, Q, on the test strip is determined from the constant current value, I, from the constant current source 106 multiplied by the time, T, from the timer 114 (Q=I*T). The charge, Q, may thereafter be converted into a BGL number with a BGL/Q look-up table stored in the memory 110. In step 620 the BGL number may be displayed on the display 118.

Figure 7:
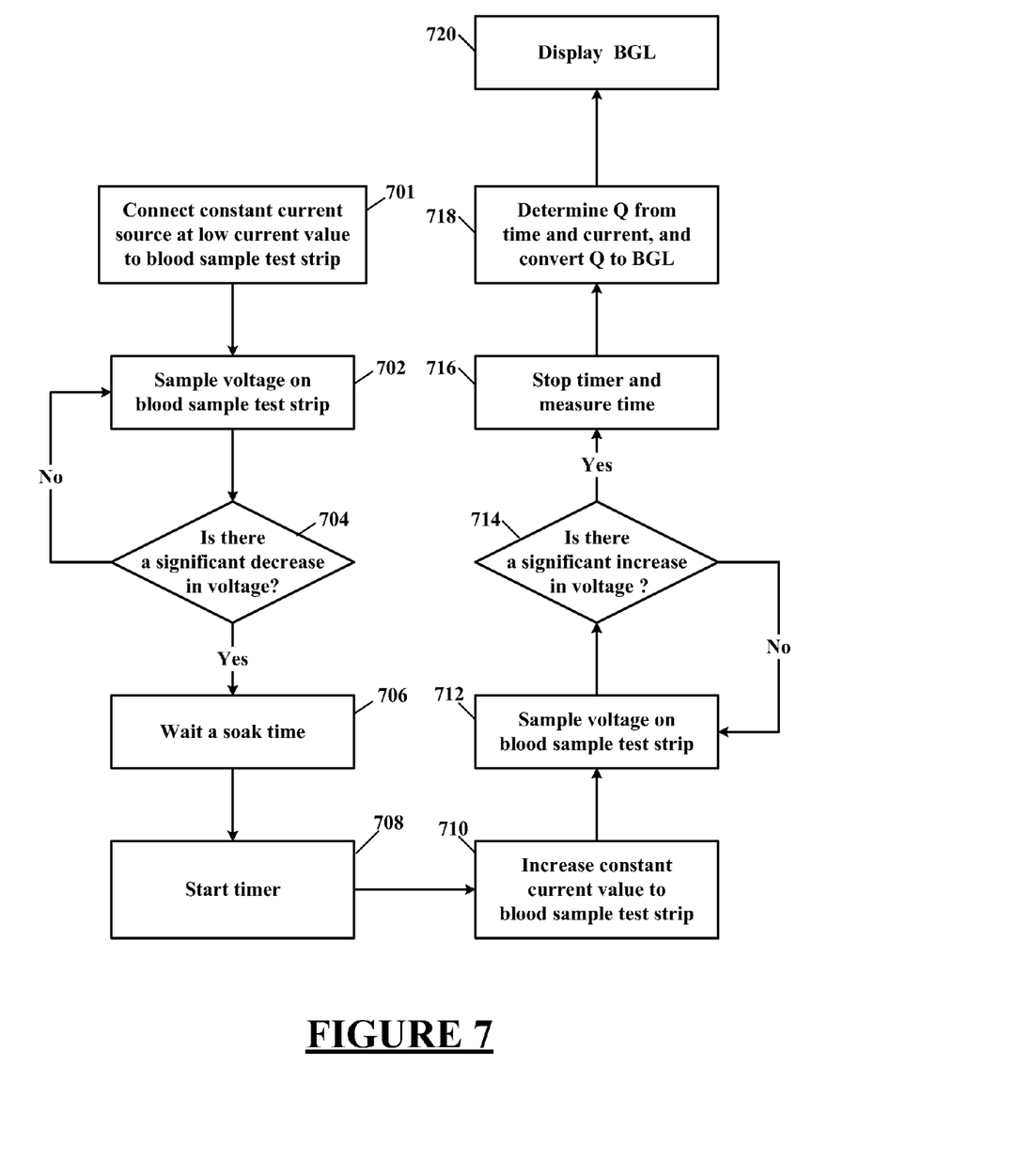
FIG. 7 illustrates a schematic flow diagram of a method for measuring blood glucose, according to yet another specific example embodiment of this disclosure.

Referring to FIG. 7, depicted is a schematic flow diagram of a method for measuring blood glucose, according to yet another specific example embodiment of this disclosure. In step 701 a constant current source 106 set to a low current value is connected to a blood sample test strip 104. In step 702 a voltage sample of the test strip 104 is taken by the ADC 112 which converts this voltage sample to a digital representation thereof, the digital processor 110 reads the digital representation and stores it into the memory 110. In step 704 a comparison is made of the voltage sample just taken to a prior sampled voltage (digital representation thereof stored in the memory 110) of the test strip 104. If there is not a significant decrease in the value of the voltage sample then another voltage sample is taken by the ADC 112. The constant current source 106 remains set to the low current value for a soak time determined in step 706. Once the soak time of step 706 is over, a timer 114 is started in step 708, and in step 710 the constant current source 106 set to a higher current value.

In step 712 another voltage sample of the test strip 104 is taken by the ADC 112 which converts this voltage sample to a digital representation thereof, the digital processor 110 reads this digital representation and stores it into the memory 110. In step 714 a comparison is made of the voltage sample just taken to a prior sampled voltage (digital representation thereof stored in the memory 110) of the test strip 104. If there is not a significant increase in the value of the voltage sample then another voltage sample is taken by the ADC 112. However, if there is a significant increase in the value of the voltage sample then in step 716 the timer 114 is stopped and the time elapsed therein is measured. In step 718 the amount of charge, Q, on the test strip is determined from the constant current value, I, from the constant current source 106 multiplied by the time, T, from the timer 114 (Q=I*T). The charge, Q, may thereafter be converted into a BGL number with a BGL/Q look-up table stored in the memory 110. In step 720 the BGL number may be displayed on the display 118.

While embodiments of this disclosure have been depicted, described, and are defined by reference to example embodiments of the disclosure, such references do not imply a limitation on the disclosure, and no such limitation is to be inferred. The subject matter disclosed is capable of considerable modification, alteration, and equivalents in form and function, as will occur to those ordinarily skilled in the pertinent art and having the benefit of this disclosure. The depicted and described embodiments of this disclosure are examples only, and are not exhaustive of the scope of the disclosure.

What is claimed is:

1. A method for measuring glucose in a blood sample, said method comprising the steps of:
   a) connecting a constant current source having a constant current value to a blood sample test strip;
   b) introducing a blood sample onto the blood sample test strip;
   c) reacting the blood sample with an enzyme in the blood sample test strip to produce a charge, Q, on the blood sample test strip;
   d) measuring a voltage on the blood sample test strip in determining a voltage value thereof;
   e) determining whether the voltage value of the voltage on the blood sample test strip has significantly decreased from a first voltage value, wherein
      e1) if the voltage value has not significantly decreased from the first voltage value then return to step d), and
      e2) if the voltage value has significantly decreased from the first voltage value then contiune to step f);
   f) disconnecting the constant current source from the blood sample test strip;
   g) waiting a soak time;
   h) starting a timer to determine a charge removal time after the soak time is over;
   i) reconnecting the constant current source to the blood sample test strip;
   j) measuring the voltage on the blood sample test strip in determining the voltage value thereof;
   k) determining whether the voltage value of the voltage on the blood sample test strip has significantly increased from a second voltage value, wherein
      k1) if the voltage value has not significantly increased from the second voltage value then return to step j), and
      k2) if the voltage value has significantly increased from the second voltage value then stop the timer and continue to step l);
   l) determining a charge value of the charge on the blood sample test strip by multiplying the charge removal time and the constant current value; and
   m) determining a blood glucose level (BGL) from the charge value.

2. The method according to claim 1, further comprising the step of displaying the BGL on a visual display.

3. The method according to claim 1, wherein the step of determining the BGL from the charge value comprises the steps of looking up the charge value in a look-up table and reading a corresponding BGL value therefrom.

4. The method according to claim 1, wherein the soak time is about one (1) second.

5. The method according to claim 1, wherein the soak time is less than one (1) second.

6. The method according to claim 1, wherein the soak time is from about one (1) second to about five (5) seconds.

7. A method for measuring glucose in a blood sample, said method comprising the steps of:
   a) connecting a constant current source having a constant current first value to a blood sample test strip;
   b) introducing a blood sample onto the blood sample test strip;
   c) reacting the blood sample with an enzyme in the blood sample test strip to produce a charge, Q, on the blood sample test strip;
   d) measuring a voltage on the blood sample test strip in determining a voltage value thereof;
   e) determining whether the voltage value of the voltage on the blood sample test strip has significantly decreased from a first voltage value, wherein
      e1) if the voltage value has not significantly decreased from the first voltage value then return to step d), and
      e2) if the voltage value has significantly decreased from the first voltage value then contiune to step f);
   f) waiting a soak time;
   g) starting a timer to determine a charge removal time after the soak time is over;
   h) increasing the constant current first value to a constant current second value;
   i) measuring the voltage on the blood sample test strip in determining the voltage value thereof;
   j) determining whether the voltage value of the voltage on the blood sample test strip has significantly increased from a second voltage value, wherein
      j1) if the voltage value has not significantly increased from the second voltage value then return to step i), and
      j2) if the voltage value has significantly increased from the second voltage value then stop the timer and contiune to step k);
   k) determining a charge value of the charge on the blood sample test strip by multiplying the charge removal time and the constant current value; and
   l) determining a blood glucose level (BGL) from the charge value.

8. The method according to claim 7, further comprising the step of displaying the BGL on a visual display.

9. The method according to claim 7, wherein the step of determining the BGL from the charge value comprises the steps of looking up the charge value in a look-up table and reading a corresponding BGL value therefrom.

10. The method according to claim 7, wherein the soak time is about one (1) second.

11. The method according to claim 7, wherein the soak time is less than one (1) second.

12. The method according to claim 7, wherein the soak time is from about one (1) second to about five (5) seconds.

13. An apparatus for measuring glucose in a blood sample, comprising:
   a blood sample test strip having an enzyme that reacts with glucose in a blood sample to produce a charge;
   an analog-to-digital converter (ADC) coupled to the blood sample test strip;
   a digital processor and memory coupled to the ADC;
   a timer for measuring a charge removal time, the timer is coupled to the digital processor;
   a constant current source having a constant current value; and
   a switch coupled between the constant current source and the blood sample test strip, and controlled by the digital processor, wherein the switch is normally closed;
   wherein when a blood sample is taken onto the blood sample test strip
      a voltage across the blood sample test strip changes from a high level to a low level,
      the switch opens thereby disconnecting the constant current source from the blood sample test strip, the switch remains open for a soak time, and after the soak time has elapsed the timer starts measuring the charge removal time and the switch closes thereby reconnecting the constant current source to the blood sample test strip;

wherein the ADC samples the voltage across the blood sample test strip until the voltage substantially increases then the timer stops measuring the charge removal time; and the digital processor calculates the charge that was on the blood sample test strip by multiplying the constant current value with the charge removal time.

14. The apparatus according to claim 13, further comprising the digital processor converting the calculated charge to a blood glucose level (BGL).

15. The apparatus according to claim 14, further comprising a display coupled to the digital processor and displaying the BGL.

16. The apparatus according to claim 14, further comprising a charge-to-BGL look-up table stored in the memory and used by the digital processor to convert the calculated charge to the BGL.

17. The apparatus according to claim 13, further comprising a constant current source having a plurality of programmable constant current values controlled by the digital processor.

18. The apparatus according to claim 13, wherein the ADC, digital processor and memory, timer, constant current source and switch are fabricated on an integrated circuit.

19. The apparatus according to claim 18, wherein the integrated circuit comprises a mixed signal analog and digital microcontroller integrated circuit.

20. The apparatus according to claim 13, wherein the digital processor is a microcontroller.

21. The apparatus according to claim 13, wherein the soak time is about one (1) second.

22. The apparatus according to claim 13, wherein the soak time is less than one (1) second.

23. apparatus according to claim 13, wherein the soak time is from about one (1) second to about five (5) seconds.

24. An apparatus for measuring glucose in a blood sample, comprising:

a blood sample test strip having an enzyme that reacts with glucose in a blood sample to produce a charge;

an analog-to-digital converter (ADC) coupled to the blood sample test strip;

a digital processor and memory coupled to the ADC;

a timer for measuring a charge removal time, the timer is coupled to the digital processor; and a constant current source coupled to the blood sample test strip and the digital processor, wherein the constant current source comprises a plurality of programmable constant current values controlled by the digital processor;

wherein the constant current source is at a low constant current value, a blood sample is taken onto the blood sample test strip, the constant current source remains at the low constant current value until a voltage across the blood sample test strip changes from a high level to a low level, then the constant current source changes to a higher constant current value and the timer starts measuring the charge removal time, and the ADC samples the voltage across the blood sample test strip until the voltage substantially increases then the timer stops measuring the charge removal time; and the digital processor calculates the charge that was on the blood sample test strip by multiplying the higher constant current value with the charge removal time.

25. The apparatus according to claim 24, further comprising the digital processor converting the calculated charge to a blood glucose level (BGL).

26. The apparatus according to claim 25, further comprising a display coupled to the digital processor and showing the BGL.

27. The apparatus according to claim 25, further comprising a charge-to-BGL look-up table stored in the memory and used by the digital processor to convert the calculated charge to the BGL.

28. The apparatus according to claim 24, wherein the ADC, digital processor and memory, timer and constant current source are fabricated on an integrated circuit.

29. The apparatus according to claim 28, wherein the integrated circuit comprises a mixed signal analog and digital microcontroller integrated circuit.

30. The apparatus according to claim 24, wherein the digital processor is a microcontroller.

31. The apparatus according to claim 24, further comprising the constant current source remains at a low constant current value for a soak time after the voltage across the blood sample test strip changes from the high level to the low level.

32. The apparatus according to claim 31, wherein the soak time is about one (1) second.

33. The apparatus according to claim 31, wherein the soak time is less than one (1) second.

34. The apparatus according to claim 31, wherein the soak time is from about one (1) second to about five (5) seconds.

* * * * *